United States Patent [19]

Hiemisch

[11] Patent Number: 5,443,522
[45] Date of Patent: Aug. 22, 1995

[54] ARTIFICIAL FOOT HAVING A LOW-POSITIONED JOINT AND A HORIZONTAL PLANTAR BUFFER

[75] Inventor: Christian Hiemisch, Duderstadt, Germany

[73] Assignee: Otto Bock Orthopaedische Industrie Besitz und Verwaltungs-Kommanditgesellschaft, Duderstadt, Germany

[21] Appl. No.: 37,163

[22] Filed: Apr. 26, 1993

[30] Foreign Application Priority Data

Mar. 27, 1992 [DE] Germany ............... 42 09 974.9

[51] Int. Cl.⁶ ............................................. A61F 2/66
[52] U.S. Cl. ............................. 623/49; 623/52; 623/53
[58] Field of Search ............... 623/55, 52, 48, 50, 623/49, 53, 47

[56] References Cited

U.S. PATENT DOCUMENTS

| | | | |
|---|---|---|---|
| 792,711 | 6/1905 | Koeber | 623/55 X |
| 817,340 | 4/1906 | Rosenkranz | 623/49 |
| 1,026,109 | 5/1912 | Morris et al. | 623/33 |
| 1,069,409 | 8/1913 | Gaines et al. | 623/52 |
| 2,439,195 | 4/1948 | Witmyer et al. | |
| 3,659,294 | 5/1972 | Glabiszewski | |
| 4,302,856 | 12/1981 | May | |
| 4,360,931 | 11/1982 | Hampton | |
| 5,064,438 | 11/1991 | Naeder | 623/55 |
| 5,112,356 | 5/1992 | Harris et al. | 623/49 |
| 5,158,570 | 10/1992 | Schey et al. | 623/52 |

FOREIGN PATENT DOCUMENTS

| | | |
|---|---|---|
| 2184210 | 12/1973 | France . |
| 0330285 | 12/1920 | Germany ............... 623/55 |
| 0390864 | 3/1924 | Germany ............... 623/55 |
| 1211354 | 2/1966 | Germany ............... 623/49 |
| 2930892 | 2/1980 | Germany . |
| 3228972 | 2/1984 | Germany . |
| 3644613 | 7/1988 | Germany . |
| 138278 | 2/1920 | United Kingdom . |

*Primary Examiner*—David H. Willse
*Attorney, Agent, or Firm*—Foley & Lardner

[57] ABSTRACT

The invention relates to an artificial foot which is essentially composed of an incompressible core, a heel wedge, an inner foot and an outer foot surrounding everything. In order to achieve a prosthetic foot for normal walking with the emphasis on comfort, the following additional characteristics are proposed in accordance with the invention: a) a low positioned joint which moves in all directions; b) the joint exhibits a virtually perpendicular bolt, the lower end of which is shaped like a condyle, and the top and sides of the condyle are covered by a bearing shell; c) at the rear facing the heel, the bolt rests on a horizontal plantar buffer, which is inserted into a space in the core open to the connecting surface and to the front, and essentially acts upon the bolt like a horizontally operating pressure spring; d) the upper end of the bolt is attached to an adapter, the bottom of which is supported directly or indirectly by the core in the front area located in front of the bolt and on the plantar buffer in the rear area behind the bolt.

21 Claims, 3 Drawing Sheets

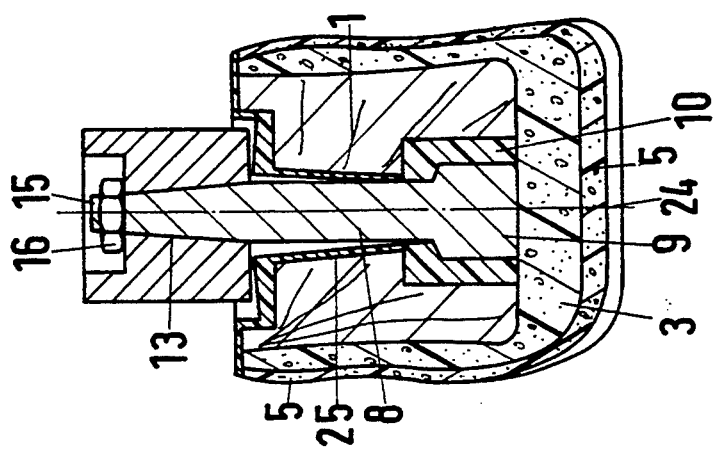
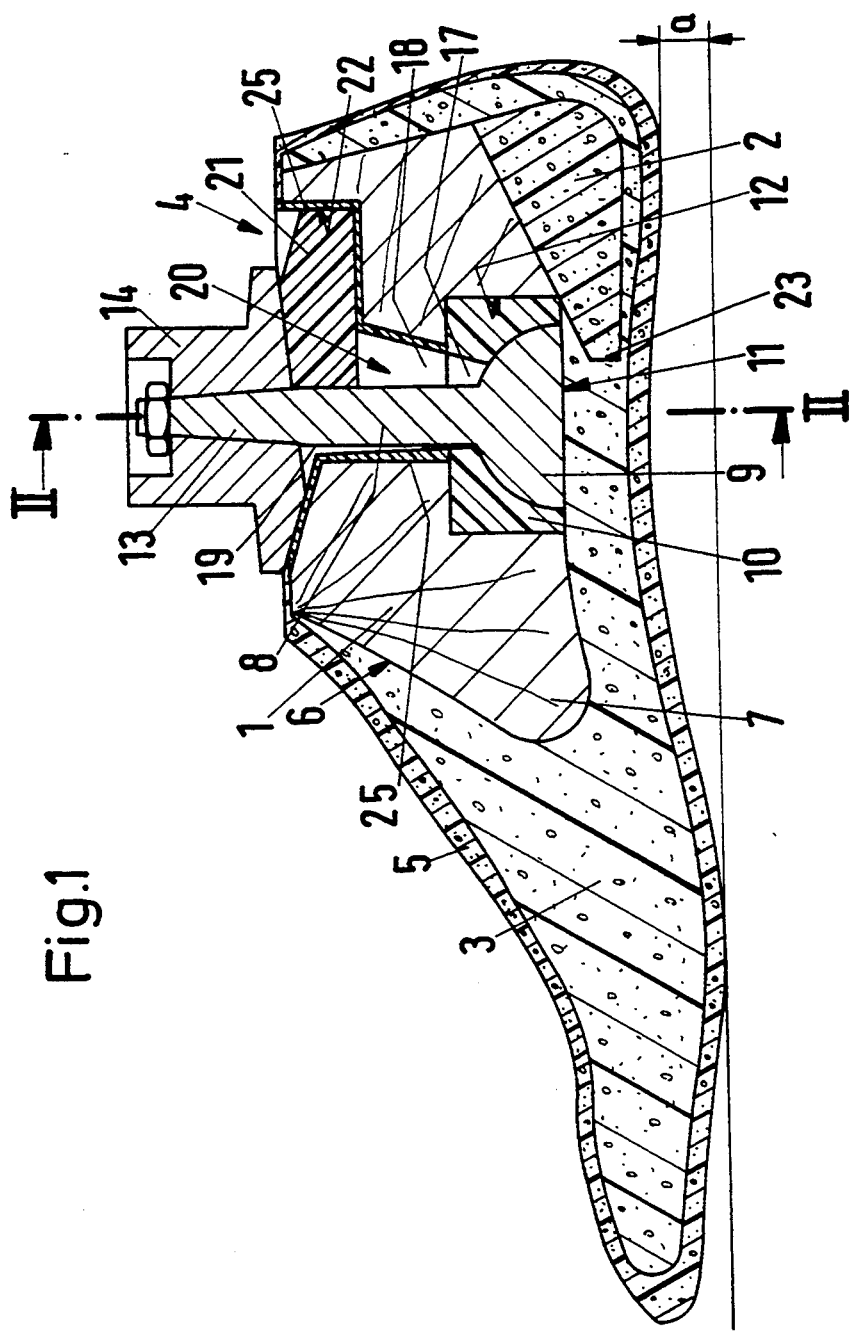

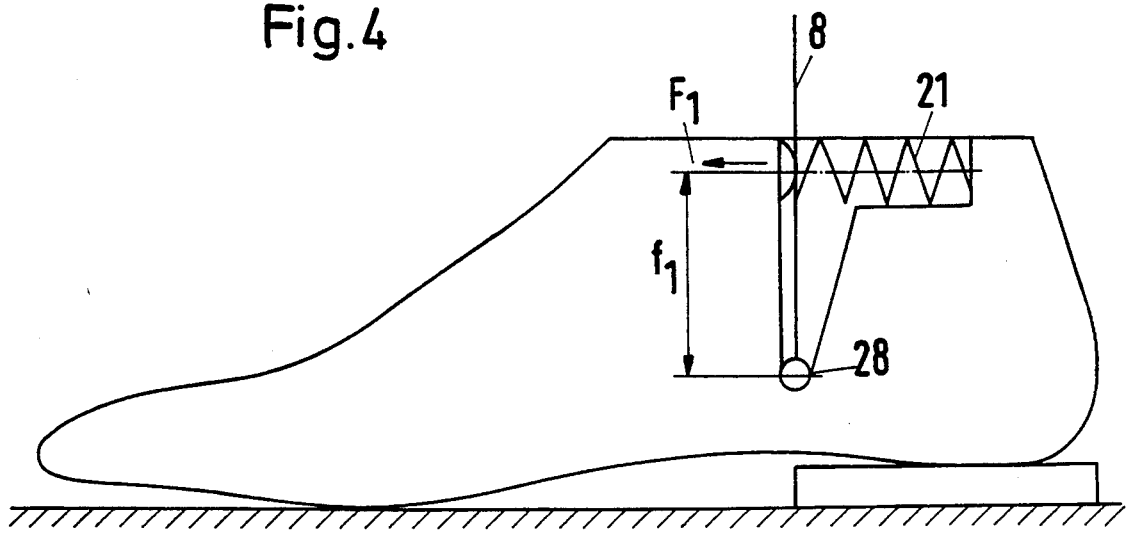

ARTIFICIAL FOOT HAVING A LOW-POSITIONED JOINT AND A HORIZONTAL PLANTAR BUFFER

BACKGROUND OF THE INVENTION

The invention relates to an artificial foot.

An embodiment of an artificial foot is described in DE-PS 36 44 613. It relates to a non-articulated foot with a connecting component resting on the upper side of the core, which can be removed in the usual way and is connected by means of a threaded bolt inserted from the bottom of the foot into a drill hole in the core of the foot and screwed into a threaded nut in the connecting component. The front of the heel wedge locks approximately with the front of the core, with the heel wedge rising backwards to over half the height of the foot. The inner foot rests solely on the front of the core and the front of the heel wedge. The outer foot wraps the inner foot, as well as the bottom and back of the heel wedge and forms a thin layer of skin in the drill hole mentioned. In this artificial foot known from the prior art, the characteristics of the gait in the second phase of the rolling movement (when the heel is lifted) are determined almost exclusively by the flexible characteristics of the inner foot. The outer foot serves solely to protect against the penetration of water and aggressive agents, as well as to provide a cosmetic appearance for the surface of the foot.

In an artificial foot in accordance with DE-PS 36 44 613, which describes a generic concept, exceeding the maximum size and/or providing less than the minimal stiffness of the heel wedge leads to the desired soft tread of the front of the foot, although with a relatively small burden on the heel. However, in contrast to its neutral status in standing, in this situation the prosthetic foot takes on a position which falls backward so much that the amputee has the feeling that he has stepped in a hole and that getting out of it requires so much energy that he will have trouble expending it for an extended period. In contrast, the foot in accordance with the present invention reacts to pressure on the heel by decreasing the angle between the lower leg and the heel, called a plantar flexion, until the front of the foot is set down, at which point the prosthetic foot assumes a position which corresponds exactly to its neutral status while standing. Therefore, in contrast to a non-articulated foot with a large and soft heel wedge, it is possible with the present invention to roll forward with the front foot without expending much energy.

In a conventional joint construction, the joint axis in the foot is located very high, often at the level of the foot connecting surface, and has only a short lever arm from the vertically-acting plantar buffer. Since, in the design in accordance with the present invention, the pivot of the joint in the foot is situated very low (preferably in the lower quarter of the height of the foot), a lever arm considerably longer than the horizontally operating plantar buffer is located in the area of the foot connecting surface, so that with the same plantar moment, the force of the plantar buffer can be smaller when constructed in accordance with the invention. The plantar buffer in accordance with the invention can therefore be designed to be weaker, which also has a positive effect on its dimensions. Because of the low positioning of the joint, there is also a cosmetic advantage: the split in the joint found in many conventional solutions behind the joint axis in neutral position and in front of the joint axis in plantar flexion disappears completely in the design in accordance with the invention.

When the prosthesis wearer is in a standing position (state of standing upright) and viewed from the side (sagittal view), the vertical line from his center of gravity lies in front of the turning point of the joint in the foot and thus produces a knee-safeguarding moment via the elastic front of the foot, to the extent that the other components of the prosthesis are also arranged in relation to each other in accordance with the rules of prosthesis construction.

The foot in accordance with the invention avoids a sharp sinking in the heel area, with the related loss of center of gravity height, that is characteristic of the non-articulated foot of the prior art. The foot in accordance with the invention assumes a horizontal position after the front of the foot is set down, while the non-articulated foot ends up in a position which falls sharply backward. Other advantages of the foot in accordance with the invention lie in the maintenance-free and extremely durable design of the joint. No further assembly or adjustment to the foot is required. For that reason, in accordance with the invention it is possible to construct the outer foot to be completely sealed at the bottom of the foot as well.

Other characteristics of the invention are discussed in greater detail in combination with further advantages of the invention on the basis of explanatory examples.

SUMMARY OF THE INVENTION

The purpose of the present invention is to create a prosthetic foot for normal walking with the emphasis on comfort.

Proceeding from an artificial foot, with
- a practically incompressible core which forms an upper connecting surface in the ankle area, the front of the core adjoining the connecting surface and extending over a base located in the instep area of the foot, which tapers down toward the front, and overall is about half as long as the entire foot;
- a heel wedge made of soft synthetic foam joined to the under side of the core;
- an inner foot connected to the front of the core and to the front end of the heel wedge, extending to the toe area and composed of a synthetic foam, and
- an outer foot which completely covers the inner foot with the exception of the upper connecting surface, constructed of a soft, easily deformable, skin forming synthetic foam layer, whose restoring force is slight compared to that of the inner foot, this purpose is accomplished in accordance with the invention-by the following characteristics:
  a) a low-positioned joint which moves in all directions;
  b) the joint exhibits a virtually perpendicular bolt, the lower end of which is shaped like a condyle and the top and sides of the condyle are covered by a bearing shell;
  c) at the rear facing the heel, the bolt rests on a horizontal plantar buffer, which is inserted into a space in the core which is open to the connecting surface and to the front, and essentially acts upon the bolt like a horizontally operating pressure spring;
  d) the upper end of the bolt is attached to an adapter, the bottom of which is supported directly or indirectly on the core in the front area located in front of the bolt and on the plantar buffer in the rear area behind the bolt.

An especially easy-to-construct joint is then achieved if the bearing shell is inserted into a corresponding space in the core which is open toward the bottom, and locks almost flush with the bottom of the core, and also if the condyle is formed by a semicircular disc, which is located in the longitudinal central plane of the foot and lies with its flat side on a level section of the inner foot.

To limit the swivelling motion of the bolt, it would be advantageous if the bolt were inserted from below through a hole in the bearing shell and an adjoining hole in the core, with the two aligned holes widening conically upward in such a way that, in the case of perpendicularly oriented bolts, a narrow wedge-shaped opening remains between the front bolt perimeter and the front wall of the holes, while a wider opening remains between the rear bolt perimeter and the rear wall of the opening.

In the foot in accordance with the invention, the dorsal swivel angle as planned for construction (the angle between the lower leg and the front of the foot) is very small compared to the plantar swivel angle (the angle between the lower leg and the heel). In addition, the medial (inner) swivel angle and the lateral (outer) swivel angle are different. The design in accordance with the invention combines the positive characteristics of an articulated foot for heel impact and the positive characteristics of a nonarticulated foot for rolling on the front of the foot. In addition, this permits a limited degree of torsion of the longitudinal axis of the leg.

The term "emphasis on comfort" used in the statement of the purpose describes a characteristic in accordance with the invention which is characterized especially by a pleasantly soft rolling in the overall standing phase of the prosthesis tread from heel impact until lifting of the tip of the foot. A behavior of the prosthetic tread emphasizing comfort in the heel impact means, for example, in the case a person whose leg has been amputated at the top, the smallest possible stiffness in the heel which still provides sufficient absorption of impact during compression of the heel wedge, but which, with a continuous gait, makes possible a rapid (promoting a sense of security in the amputee), but not hard placement of the front of the foot, without needing to generate a noticeable stretching of the hips to compensate for the knee-bending effect of the backward force transmitted from the foot to the lower leg.

To achieve the foregoing advantage and in accordance with the purpose of the invention, as embodied and broadly described herein, an artificial foot comprises a practically incompressible core which forms an upper connecting surface in an ankle area, a front of the core adjoining the connecting surface and extending over a base located in an instep area of the foot, which core tapers down toward the front, and overall is about half as long as the entire foot; a heel wedge made of soft synthetic foam joined to the under side of the core; an inner foot connected to the front of the core and to a front end of the heel wedge, extending to a toe area and composed of a synthetic foam; an outer foot which completely covers the inner foot except the upper connecting surface, constructed of a soft, easily deformable, skin-forming synthetic foam layer, whose restoring force is slight compared to that of the inner foot; and a low-positioned joint which moves in all directions; wherein the joint includes a virtually perpendicular bolt, a lower end of which is shaped like a condyle and a top and sides of the condyle are covered by a bearing shell; wherein a rear facing the heel, the bolt rests against a horizontal plantar buffer, which buffer is inserted into a space in the core which is open to the connecting surface and to the front, and essentially acts upon the bolt like a horizontally operating pressure spring; and wherein an upper end of the bolt is attached to an adapter, a bottom of which adapter is supported on the core in the front area located in front of the bolt and on the plantar buffer in the rear area behind the bolt.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention serving as examples, and, together with the general description given above and the detailed description of the preferred embodiments given below, serve to explain the principles of the invention.

FIG. 1 shows a longitudinal cross-section of an artificial foot equipped with a joint;

FIG. 2 shows a cross-section along line II/II in FIG. 1;

FIG. 4 shows a schematic presentation to illustrate the operation of a plantar buffer, in accordance with the invention, upon a bolt of the foot joint.

DETAILED DESCRIPTION OF THE PREFERRED EMBODIMENTS

Figure 3:
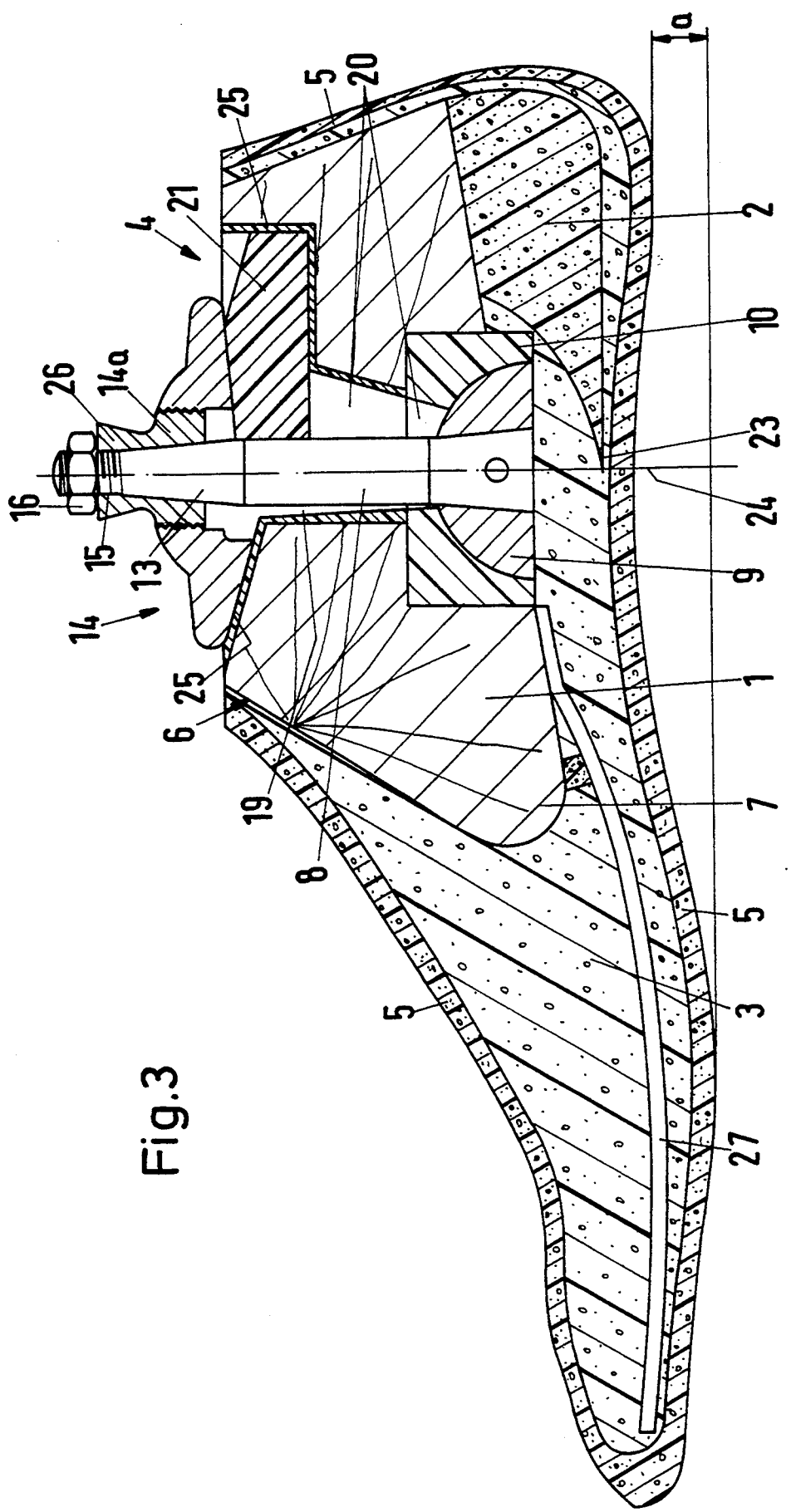
FIG. 3 shows a modified version in a larger scale illustrated as for FIG. 1.

The artificial foot shown in FIGS. 1 through 3 essentially consists of a core 1, a heel wedge 2 adjoining its under side, an inner foot 3, and an outer foot 5 which completely surrounds these components with the exception of an upper connecting surface 4. In addition, provision is made for a low-positioned joint which moves in all directions.

The virtually incompressible core 1 is preferably composed of poplar wood, with a specific mass of 0.48 g/cm$^3$, for example. The core 1 extends on its front side 6 to meet connecting surface 4 via the base 7, which tapers downward at the front in the instep area of the foot. The overall length of the core 1 corresponds preferably to 50% to 60% of the entire length of the foot.

The joint has a virtually vertical bolt 8, the lower end of which is designed like a condyle, and is covered on the sides and top by a bearing shell 10. The condyle 9 is in the form of a semi-circular disc which lies along the longitudinal central level of the foot and has a flat side 11 which rests on a level section of the inner foot 3. The bearing shell 10 is a synthetic component with a hardness of 80 to 90 Shore, and is inserted in a corresponding hollow space 12 in the core 1 which is open below and is closely aligned with the bottom of the core 1. The upper end of the bolt 8 is constructed as a cone 13 which is inserted into a corresponding inner cone of an adapter 14 and has a tensioning thread 15 on its free end, which is screwed into the tensioning nut 16 supported by the adapter 14. The bolt 8 is inserted from below into a hole 17 in the bearing shell 10 and through a connecting hole 18 in the core 1. The two aligned holes 17 and 18 open conically upward in such a way that, in the case of the perpendicularly oriented bolt 8, a narrow wedge-shaped opening 19 remains between the front perimeter and the front wall of the holes 17, 18, while a wider opening 20 remains between the rear bolt perimeter and the rear wall of the hole.

The bolt 8 rests, with its rear side facing the heel, on the horizontal plantar buffer 21, which is inserted in a space 22 in the core 1 which is open toward the connecting surface 4 and toward the front, and acts upon bolt 8 by means of a pressure spring which essentially operates horizontally. The plantar buffer is constructed as a synthetic component with a specific mass of about 0.4 to 0.5 g/cm$^3$. The adapter 14 rests directly or indirectly on the core 1, with its under side in the area in front of the bolt 8, and with the rear area behind the bolt 8 upon the plantar buffer 21, the upper side of which rises slightly toward the back of the foot.

The heel wedge 2 is composed of a soft synthetic foam with a specific mass of about 0.2 to 0.4 g/cm$^3$, rises to the rear to a height of about the area of the condyle 9 and extends with its forward side or front end 23 to underneath the rear area of the bearing shell 10 and at most to the bolt axis 24.

The inner foot 3 is composed of a synthetic foam with a specific mass of about 0.5 to 0.8 g/cm$^3$, adjoins the front side 6 of the core 1 and the front end 23 of the heel wedge, extends to the area of the toes and covers the upper connecting surface 4, the space 22 for the plantar buffer 21 and the walls of the hole 18 in the core 1 with a thin skin 25. When the foot is manufactured, the bearing shell 10 is first inserted into its assigned space 12 in core 1. Then the bolt 8 is shoved in from below, until the condyle 9 lies against the bearing shell 10. Then the heel wedge is attached and the combination of parts consisting of the core 1, the bearing shell 10 with the condyle 9 and heel wedge 2 are covered in foam to form the inner foot 3, during which the thin skin 25 described above is created. The core 1 and heel wedge 2 are thus covered completely by inner foot 3, with the exception of the surface lying between the core 1 and the heel wedge 2.

The outer foot 5 is constructed using a soft, easily deformable, skin-forming layer of synthetic foam, whose restoring force is small in comparison to the restoring force of the inner foot 3, and which has a specific mass of 0.4 to 0.6 g/cm$^3$. This outer foot completely covers the inner foot 3, leaving only the connecting surface 4 open.

FIG. 1 shows that the bolt 8 can move only very slightly forward, but considerably more backwards; the swing is performed by means of an elastic reshaping of the inner foot 3 achieved by the flat side 11 of the condyle 9 and the swing to the back takes place in addition against the elastic tension of the plantar buffer 21. The plantar flexion in the sagittal plane, i.e., the swing of bolt 8 within the plane of projection of FIG. 1, amounts to a maximum of 15'. The sagittal plane is a plane lying perpendicular to the direction of the gait. The elasticity of the material of the bearing shell 10 and of the inner foot 3 which wraps around the condyle 9 also produces a lateral movement of the joint in a vertical frontal plane lying transverse to the direction of the gait, with the swivelling area in the lateral direction smaller than that in the medial direction. The elasticity of the material which forms the bearing shell also permits torsion of the foot along the longitudinal axis of the leg.

FIG. 3 shows an artificial foot which differs in some details from the one in FIG. 1; each of the modifications can be made individually.

An initial alteration is the two-part construction of the adapter 14, in which a central component 14a is inserted; the latter is provided with an inner cone for the cone 13 of bolt 8, and has on its tip a pyramidal connecting piece 26 for an adjustable connection with the lower leg. A corresponding adjustable connection is shown by DE-PS 19 22 619, for example.

Another modification is the two-part construction of the bolt 8 and the condyle 9, which are joined to each other by a shear pin or a similar device to prevent them from turning.

Another modification is the optional use of a reinforcing strap 27, which can be made of a synthetic strip and is fastened to the under side of the forward base 7 of the core 1, and extends to the area of the toes. This reinforcement of the front of the foot can serve to counter the danger of crack formation on the sole of the foot as a result of longitudinal over-extension, which can arise when synthetic foams of specific weights are used on the bottom edge of the area in use.

The artificial foot in accordance with the illustrated explanatory examples is normally worn with a shoe, not illustrated in any detail, the heel height a of which is shown in FIGS. 1 and 3.

The essential advantages of the foot in accordance with the invention lie in combining the positive characteristics of an articulated foot for heel impact, with the positive characteristics of a non-articulated foot for the roll over on to the front of the foot, in a differentiated transverse mobility in medial and lateral directions and in limited torsion along the longitudinal axis of the leg.

FIG. 4 clarifies the plantar moment exerted upon the bolt 8 the plantar buffer 21 is shown as a horizontal pressure spring whose back end lies on the rear wall of the space 22 and whose front end rests on bolt 8. The spring force of plantar buffer 21 is stated as $F_l$, while the lever arm to the schematically indicated joint axis 28 is designated as $f_1$. In contrast to conventional solutions, because of the considerably longer lever arm $f_1$, the tension $F_1$ of the plantar buffer 21 can be smaller to produce the same plantar moment; as a result, the plantar buffer 21 can be of weaker construction.

FIG. 4 shows the actual relationships only in simplified form. For in a swing to the back the swing of the section of the bolt 8 lying on the plantar buffer 21 takes place in the arc of a circle around the center of the joint; the operation of the plantar buffer in a compressed state is not exactly horizontal but is oriented at a tangent to this arc. This divergence is so slight, however, that the assumption of a pressure spring with an essentially horizontal operation can be made.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An artificial foot comprising:
   a practically incompressible core which forms an upper connecting surface in an ankle area, a front of the core adjoining the connecting surface and extending over a base located in an instep area of the foot, which tapers downwardly toward the front, and overall is about half as long as the entire foot;

a heel wedge made of soft synthetic foam joined to an under side of the core;

an inner foot connected to the front of the core and to a front end of the heel wedge, extending to a toe area and composed of a synthetic foam; and an outer foot which completely covers the inner foot with the exception of the upper connecting surface, constructed of a soft, easily deformable, skin-forming synthetic foam layer, whose restoring force is slight compared to that of the inner foot; and a low-positioned joint which moves in all directions;

wherein the joint includes a virtually perpendicular bolt, a lower end of which is shaped like a condyle and a top and sides of the condyle are covered by a bearing shell;

wherein at the rear facing the heel, the bolt rests against a horizontal plantar buffer, which buffer is inserted into a space in the core which is open to the connecting surface and to the front, and which buffer is configured to essentially act upon the bolt like a horizontally operating pressure spring; and wherein an upper end of the bolt is attached to an adapter, a bottom of which adapter is supported on the core in a front area located in front of the bolt and on the plantar buffer in a rear area behind the bolt.

2. An artificial foot in accordance with claim 1, wherein the front end of the heel wedge extends only until under an area of the joint.

3. An artificial foot in accordance with claim 2, wherein the front end of the heel wedge extends no farther than a vertical axis of the bolt.

4. An artificial foot in accordance with claim 1, wherein the bearing shell is set in a corresponding recess in the core which opens to below and locks almost flush with an underside of the core.

5. An artificial foot in accordance with claim 1 wherein the bolt is inserted from below through a hole in the bearing shell and an adjoining aligned hole in the core, with the two aligned holes widening conically upward in such a way that, after the vertically oriented bolt is inserted, a narrow wedge-shaped opening remains between a front perimeter of the bolt and a front wall of the holes, while a wider opening remains between a rear bolt perimeter and a rear wall of the adjoining hole.

6. An artificial foot in accordance with claim 1, wherein the condyle is formed by a semi-circular disc, which lies in a central longitudinal plane of the foot and rests with its flat side on a flat section of the inner foot.

7. An artificial foot in accordance with claim 1, wherein the upper end of the bolt is constructed as a cone which is inserted into a corresponding inner cone of the adapter and has a tensioning thread on its free end, which is screwed into a tensioning nut supported by the adapter.

8. An artificial foot in accordance with claim 1, wherein the adapter has a pyramid-shaped connecting component for an adjustable connection with a lower leg.

9. An artificial foot in accordance with claim 1, wherein the plantar buffer is a synthetic component with a specific mass in a range of 0.4 to 0.5 $g/cm^3$.

10. An artificial foot in accordance with claim 1, wherein the heel wedge has a specific mass in a range of 0.2 to 0.4 $g/cm^3$.

11. An artificial foot in accordance with claim 1, wherein the inner foot has a specific mass of 0.5 to 0.8 $g/cm^3$.

12. An artificial foot in accordance with claim 1, wherein the outer foot has a specific mass in a range of 0.4 to 0.6 $g/cm^3$.

13. An artificial foot in accordance with claim 1, wherein the bearing shell is a synthetic component with a hardness in a range of 80 to 90 shore.

14. An artificial foot in accordance with claim 1, wherein the plantar flexion is a maximum of fifteen degrees in a sagittal plane.

15. An artificial foot in accordance with claim 13, wherein an elasticity of the material of the bearing shell and of the inner foot which wraps around the condyle produces a lateral movement of the joint in a perpendicular frontal plane lying transverse to the direction of the gait.

16. An artificial foot in accordance with claim 1, wherein a swivelling area in a lateral plane is smaller than in a medial plane.

17. An artificial foot in accordance with claim 15, wherein the elasticity of the material which forms the bearing shell also permits torsion of the foot along a longitudinal axis of a leg to which the foot is attached.

18. An artificial foot in accordance with claim 1, wherein a reinforcing strap, extending to an area of the toes, is fastened to an under side of the base of the core.

19. An artificial foot in accordance with claim 1, wherein the inner foot is foamed completely around the core and the heel wedge.

20. An artificial foot in accordance with claim 15, wherein the inner foot covers the upper connecting surface, the space for the plantar buffer and walls of an adjoining hole in the core with a thin skin.

21. An artificial foot in accordance with claim 1, wherein the outer foot is constructed to be completely sealed on the underside of the foot as well.

* * * * *

UNITED STATES PATENT AND TRADEMARK OFFICE
CERTIFICATE OF CORRECTION

PATENT NO. : 5,443,522
DATED : August 22, 1995
INVENTOR(S) : Christian Hiemisch

It is certified that error appears in the above-indentified patent and that said Letters Patent is hereby corrected as shown below:

On the title page, item [22], change "Apr." to --Mar.--.

Signed and Sealed this

Twenty-fourth Day of October, 1995

*Attest:*

BRUCE LEHMAN

*Attesting Officer*     Commissioner of Patents and Trademarks